US008303556B2

(12) United States Patent
White

(10) Patent No.: US 8,303,556 B2
(45) Date of Patent: Nov. 6, 2012

(54) DEVICE FOR MEN TO MANAGE THE INVOLUNTARY LOSS OF BLADDER CONTROL

(76) Inventor: Wayne White, Santa Claus, IN (US)

( * ) Notice: Subject to any disclaimer, the term of this patent is extended or adjusted under 35 U.S.C. 154(b) by 322 days.

(21) Appl. No.: 12/590,787

(22) Filed: Nov. 13, 2009

(65) Prior Publication Data

US 2010/0125260 A1    May 20, 2010

Related U.S. Application Data

(60) Provisional application No. 61/199,298, filed on Nov. 14, 2008.

(51) Int. Cl.
*A61F 5/44* (2006.01)
*A61B 19/00* (2006.01)
*A47K 11/00* (2006.01)

(52) U.S. Cl. .......................... 604/349; 604/356; 4/144.3
(58) Field of Classification Search .................. 604/356, 604/358, 349; 4/144.3
See application file for complete search history.

(56) References Cited

U.S. PATENT DOCUMENTS

| 2,586,674 | A | * | 2/1952 | Lonne | 128/844 |
|---|---|---|---|---|---|
| 3,613,123 | A | * | 10/1971 | Langstrom | 4/144.3 |
| 4,387,726 | A | * | 6/1983 | Denard | 600/573 |
| 4,668,229 | A | * | 5/1987 | Fago et al. | 604/327 |
| 4,790,835 | A | * | 12/1988 | Elias | 604/349 |
| 4,838,883 | A | * | 6/1989 | Matsuura | 604/349 |
| 4,863,448 | A | * | 9/1989 | Berg | 604/349 |
| 4,886,509 | A | * | 12/1989 | Mattsson | 604/349 |
| 4,984,582 | A | * | 1/1991 | Romaniszyn et al. | 128/844 |
| 5,009,649 | A | * | 4/1991 | Goulter et al. | 604/351 |
| 5,065,459 | A | * | 11/1991 | Tjahaja et al. | 4/144.2 |
| 5,084,037 | A | * | 1/1992 | Barnett | 604/349 |
| 5,112,324 | A | * | 5/1992 | Wallace | 604/349 |
| 5,284,159 | A | * | 2/1994 | Wilk | 128/844 |
| 5,300,052 | A | * | 4/1994 | Kubo | 604/349 |
| 5,478,334 | A | * | 12/1995 | Bernstein | 604/353 |
| 5,618,277 | A | * | 4/1997 | Goulter | 604/349 |
| 5,695,485 | A | * | 12/1997 | Duperret et al. | 604/349 |
| 5,742,948 | A | * | 4/1998 | Cicio | 4/144.3 |
| 6,406,462 | B1 | * | 6/2002 | Johnson | 604/327 |
| 6,419,665 | B1 | * | 7/2002 | Cohen | 604/349 |
| 6,530,909 | B1 | * | 3/2003 | Nozaki et al. | 604/349 |
| 6,569,135 | B1 | * | 5/2003 | Mula | 604/349 |
| 6,632,204 | B2 | * | 10/2003 | Guldfeldt et al. | 604/349 |
| 6,732,384 | B2 | * | 5/2004 | Scott | 4/144.3 |
| 7,066,920 | B1 | * | 6/2006 | Mula | 604/349 |
| 7,879,016 | B2 | * | 2/2011 | Mandzij et al. | 604/335 |

(Continued)

*Primary Examiner* — Susan Su
(74) *Attorney, Agent, or Firm* — Gary K. Price

(57) ABSTRACT

A device for men to manage the involuntary loss of bladder control, the device includes an upper portion integral to a lower portion, wherein the lower portion defines a retention body having a lower opening to access an inner chamber sized and shaped to accommodate the insertion of a male penis. The upper portion defines an upper hood having an open position and a closed position. A replaceable absorbent member is disposed on an interior of the upper portion, and an attachment member releasably secures the upper portion to the retention member such that the upper portion is in the closed position. The device further consists of a first layer having a plurality of vent holes positioned along the length and width of the first layer and, a second layer having a plurality of vent holes positioned along the length and width of the second layer. A plurality of dimples are sandwiched between the first and second layers that form a separation between the layers and provides ventilation to the inner chamber.

11 Claims, 3 Drawing Sheets

U.S. PATENT DOCUMENTS

| | | |
|---|---|---|
| 2004/0087921 A1* | 5/2004 | Guldfeldt et al. ............. 604/349 |
| 2004/0106909 A1* | 6/2004 | Browning ..................... 604/349 |
| 2006/0122568 A1* | 6/2006 | Elson et al. ................... 604/352 |
| 2006/0229576 A1* | 10/2006 | Conway et al. ............... 604/349 |
| 2009/0069765 A1* | 3/2009 | Wortham ...................... 604/349 |
| 2009/0105675 A1* | 4/2009 | Romero ........................ 604/349 |
| 2011/0054427 A1* | 3/2011 | Kobren et al. ................ 604/349 |
| 2011/0054428 A1* | 3/2011 | Hill .............................. 604/349 |

* cited by examiner

DEVICE FOR MEN TO MANAGE THE INVOLUNTARY LOSS OF BLADDER CONTROL

CROSS REFERENCES TO RELATED APPLICATIONS

U.S. Provisional Application for Patent No. 61/199,298, filed Nov. 14, 2008, with title "Device for Men to Manage the Involuntary Loss of Bladder Control" which is hereby incorporated by reference. Applicant claim priority pursuant to 35 U.S.C. Par. 119(e)(i).

STATEMENT AS TO RIGHTS TO INVENTIONS MADE UNDER FEDERALLY SPONSORED RESEARCH AND DEVELOPMENT

Not Applicable.

BACKGROUND OF THE INVENTION

1. Field of the Invention

The invention relates generally to managing the involuntary loss of bladder control and more particularly to a device that is worn by men to manage incontinence without embarrassment and with dignity and discreteness.

2. Brief Description of Prior Art

Urinary incontinence is an involuntary leaking of urine and is a widespread problem for both men and women of all ages. One symptom experienced by men, is after they finish urinating and they seem to have emptied their bladder, they continue to pass small amounts of urine and experience urine leakage. As a result, they can experience the embarrassment of small but visually noticeable wet spots adjacent the flies' area of their trousers.

Many men attempt to train the muscles in the pelvic floor but too many continue to have problems with urine leakage as described. Many different solutions to this problem have been tried. However, they often involve complicated mechanical steps that are prone to malfunction. Further, these prior art devices lack discreteness. Likewise, the prior art includes absorbent devices that disadvantageously rely on providing a large area of absorbent, usually in the form of pants or diapers. Not only is such an arrangement uncomfortable, it requires involved procedures for applying and removing the device.

Unfortunately, the social stigma and embarrassment associated with urinary incontinence can contribute greatly to the distress, depression, isolation and social withdrawal experienced by some affected individuals. Accordingly, there is a need for an improved way for a male to manage his incontinence without embarrassment and with dignity and discreteness so that he may continue to lead an active life and enjoy a high quality of life.

As will be seen from the subsequent description, the preferred embodiments of the present invention overcome shortcomings of the prior art.

SUMMARY OF THE INVENTION

A device for men to manage the involuntary loss of bladder control. The device includes an upper portion integral to a lower portion. The upper and lower portions consist of a first layer and a second layer, of preferably, a soft, elastic material, each layer having a plurality of vent holes selectively positioned along the length and width of the device for ventilation. The lower portion defines a retention body having a lower opening to access an inner chamber sized and shaped to accommodate the assertion of the penis therethrough.

The upper portion defines an upper hood portion having an open position and a closed position so that the user, when needing to urinate, can simply and quickly urge the upper head portion to its open position thereby exposing the head of the penis while the shaft of the penis remains enveloped in the retention body. Once urinating is completed, the user can simply re-direct the upper hood portion to its closed position without again, disturbing the retention body.

The interior of the hood includes a replaceable absorbent member. The absorbent member can be removed and replaced from the upper hood without the necessity of having to remove the retention body. An end of the upper hood portion can further include an attachment portion that releasably secures the upper hood portion to the retention body (closed position).

DESCRIPTION OF THE PREFERRED EMBODIMENT

In accordance with the present invention, a device for men to manage the involuntary loss of bladder control is disclosed. The device is primarily directed to men that experience small amounts of urine leakage after urinating. Specifically, the device is an elastic apparatus that receives the male member and includes an absorbent portion to collect any urine leakage thereby avoiding the embarrassing wet spots previously described. In the broadest context, the device for men to manage the involuntary loss of bladder control of the present invention consists of components configured and correlated with respect to each other so as to attain the desired objective.

Figures 1, 2:
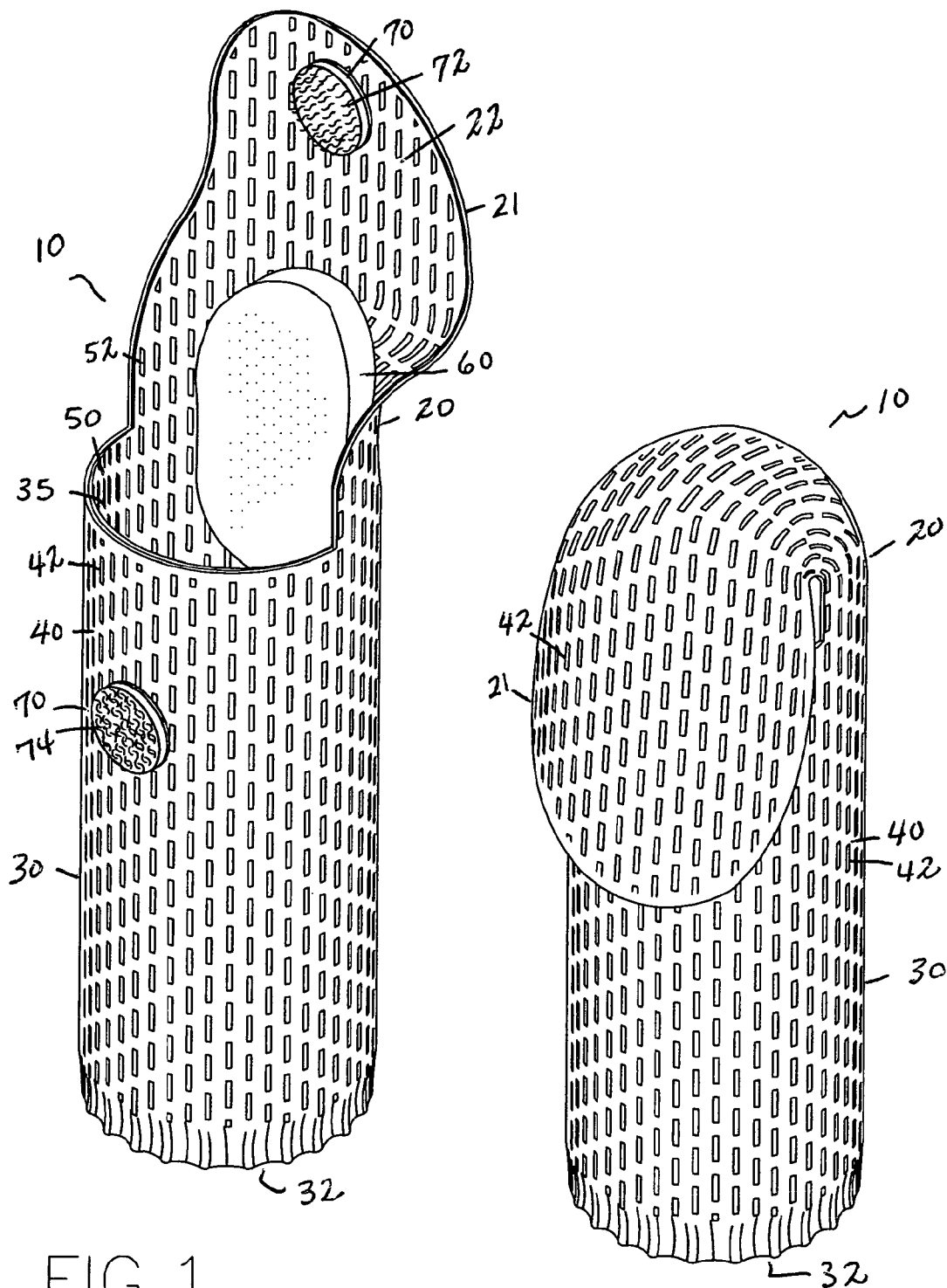
FIG. 1 is a perspective view of the present invention, a device for men to manage the involuntary loss of bladder control, in its open position.
FIG. 2 is the device of FIG. 1 in its closed position.

FIG. 1 illustrates a preferred embodiment of a device for men to manage the involuntary loss of bladder control made in accordance with the present invention. The device depicted by numeral 10, generally includes an upper portion 20 and a lower portion 30 integral to the upper portion 20. The lower portion 30 defines a retention body having a lower opening 32 to access an inner chamber 35 sized and shaped to accommodate the insertion of the penis (not shown) therethrough. As will be further described, the device 10 has a first layer 40 and a second layer 50, each layer having a plurality of vent holes positioned along the length and width of the device 10 for ventilation.

Figure 3:
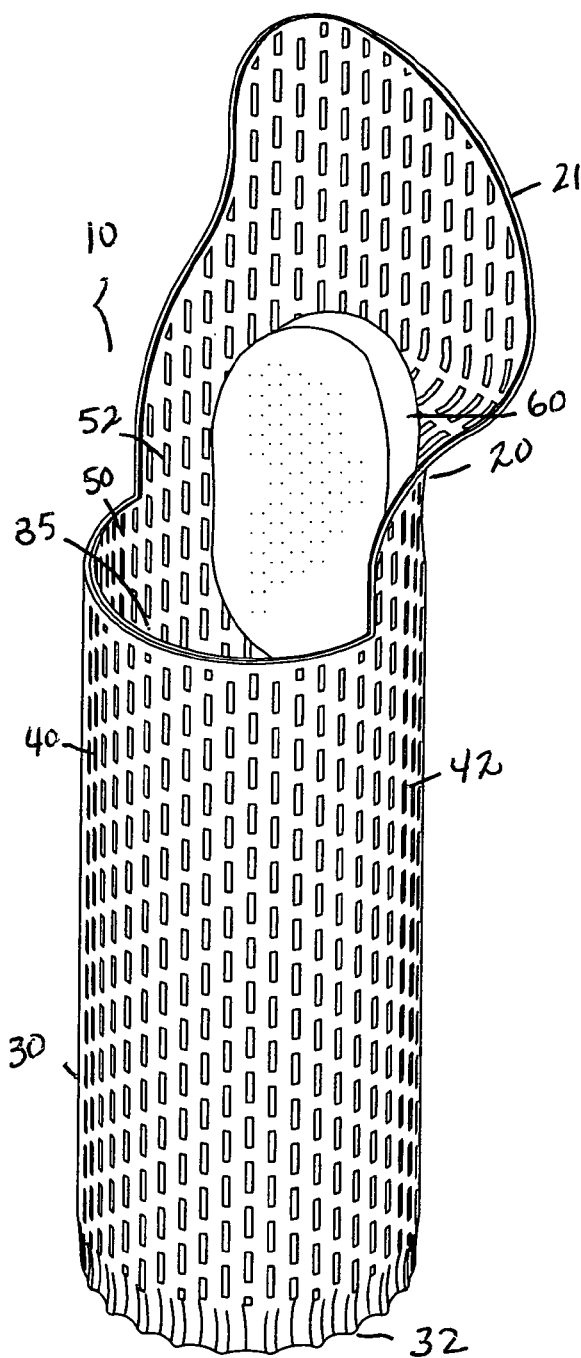
FIG. 3 is the device of FIG. 1 without the attachment portion.

The upper portion 20 defines an upper hood 21 having an open position as shown in FIGS. 1 and 3 and a closed position as shown in FIG. 2. In application, when the user needs to urinate, the user can simply and quickly urge the upper hood 21 to its open position (FIG. 1) thereby exposing the head of the penis (not shown) while the shaft of the penis (not shown) remains enveloped in the retention body 30. Once urinating is completed, the user can simply redirect the upper hood 21 to its closed position (FIG. 2) without again, disturbing the retention body.

As illustrated in FIGS. 1 and 3, the device 10 further includes a replaceable absorbent member 60 disposed on the interior 22 of the upper hood 21. Access to the absorbent member 60 is achieved when the upper portion 20 is in its open position as shown. The absorbent member 60 can then be removed and replaced from the upper portion 20 without the necessity of having to remove the retention body 30.

As shown in FIG. 1, the device 10 can further include an attachment portion 70 that releasably secures the upper hood 21 to the retention body 30 in the closed position. More particularly, the attachment portion 70 is preferably a hook-and-loop connector, such as VELCRO®(Velcro Industries B.V. LLC, Netherlands). As illustrated in FIG. 1, the attachment portion 70 may have a hook fastener 72 attached to the interior 22 of the upper hood 21 while the outer surface of the lower portion 30 may have a loop fastener 74 disposed thereon for connection with hook fastener 72. This variation on connector mechanism is intended to be illustrative and not intended to be limiting in any way.

As shown in the drawings, the first layer 40 of the device 10 includes a plurality of vent holes 42 positioned along the length and width of the first layer 40 of the device 10. Likewise, the second layer 50 includes a plurality of vent holes 52 positioned along the length and width of the second layer 50.

Figure 4:
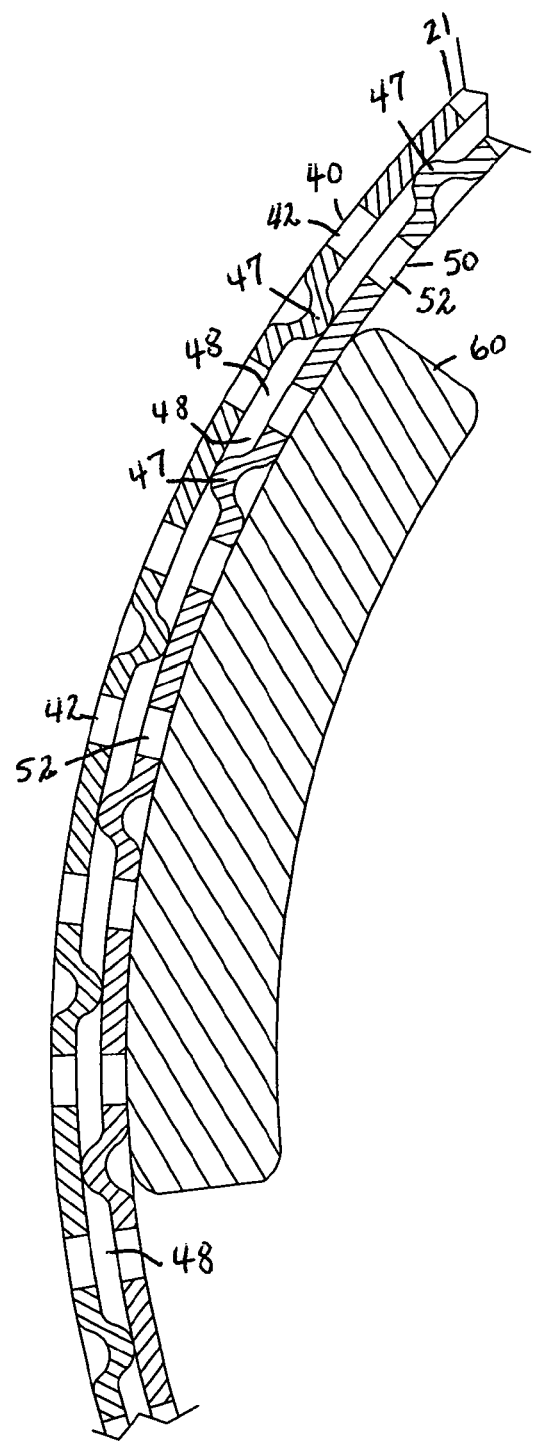
FIG. 4 shows a sectional view of the device of FIG. 1.

FIG. 4 shows a sectional view of the device 10. Preferably, the first and second layers 40, 50 include a plurality of dimples 47 selectively positioned and sandwiched between the first and second layers 40, 50. The dimples 47 cause a separation 48 between the layers 40, 50 and likewise between the vent holes 42 and 52 such to promote air circulation and ventilation between the layers 40, 50 and to allow air or ventilation to the inner chamber 35 of the lower portion 30 and the interior of the upper portion 20. As illustrated in FIG. 4, the dimples 47 are preferably equally spaced apart and again, form a continuous separation 48 between the layers 40, 50.

As should be understood, the upper hood 21 is designed so that the user, when needing to urinate, can simply urge the upper portion 20 to its open position by releasing the attachment portion 70 as described, thereby exposing the head of the penis from the upper hood 21 while the shaft of the penis remains enveloped in the lower portion 30. In this regard, the head of the penis is advantageously positioned from the upper hood 21. Once urinating is completed, the user can simply re-direct the head of the penis into the upper hood 21 without again, disturbing the lower portion 30, and then re-attaching the attachment portion 70 as described.

As illustrated, and as should be understood, the device 10 including the lower portion 30 and upper hood 21 defines a generally cylindrical inner diameter surface interior for engaging the male. The inner chamber 35 of the lower portion 30 can receive the penis therein through the lower opening 32 before securing the attachment portion 70 as described. The inner chamber 35 of the lower portion 30 envelopes the shaft of the penis and is in fluid communication with the plurality of vent holes 42, 52.

The interior 22 of the upper hood 21 includes the replaceable absorbent member 60 that is releasably positioned therein. The absorbent member 60 is positioned as an absorbing "shield" between the head of the penis and the user's trousers in order to collect any leakage that may occur once the upper hood 21 is re-attached in the closed position. As should be understood, the absorbent member 60 can be removed and replaced from the upper hood 21 without the necessity of having to remove the lower portion 30.

The illustrative embodiment was designed for one-handed application. The inner chamber 35 of the lower portion 30 provides a good anti-slip, fairly high-friction contact which stably maintains the retention body lower portion 30 on the penis.

In applying the invention as described, the lower portion 30 is installed on the penis by inserting the penis through the lower opening 32 into the inner chamber 35 of the device 10 in a circumferential fashion about the surface of the entire penis. This is in contrast to a condom, which is applied by unrolling materially longitudinally from the tip to the base of the penile shaft.

Preferably, the layers 40, 50 of the device 10 is constructed of a lightweight, elastic or light rubber absorbent material however, other materials are also possible as long as the selected material provides comfort, sufficient strength, absorbability and durability for the embodiment disclosed.

Figure 5:
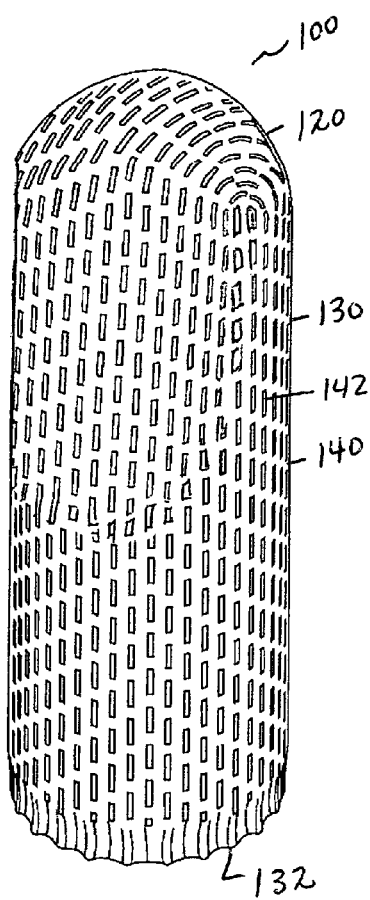
FIG. 5 is an alternate embodiment of the present invention, a device for men to manage the involuntary lost of bladder control.
Figure 6:
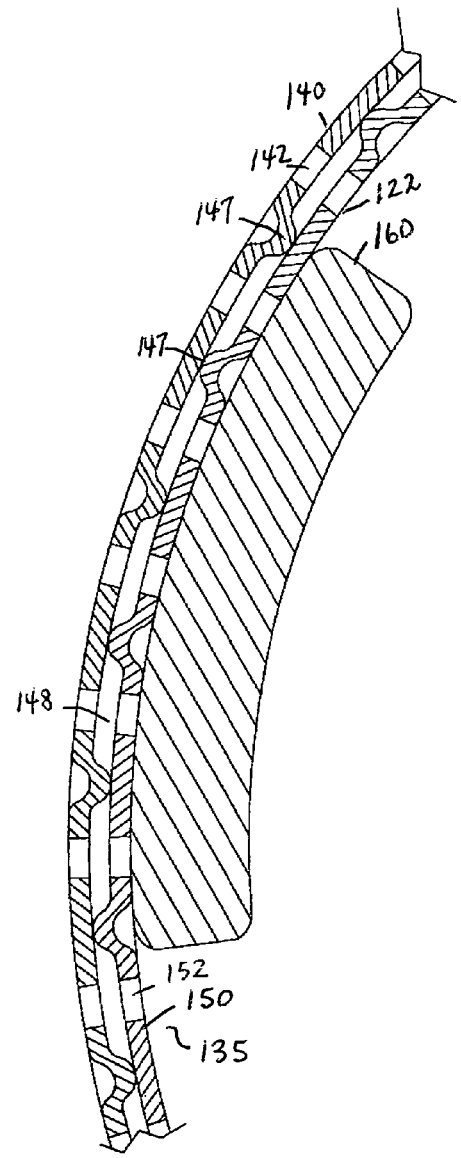
FIG. 6 shows a sectional view of the device of FIG. 5.

FIGS. 5 and 6 illustrate an alternate embodiment of the present invention, a device for men to manage the involuntary loss of bladder control, depicted by numeral 100. The device 100 generally includes a retention body 130 having a lower opening 132 to access an inner chamber 135 sized and shaped to accommodate the insertion of the penis (not shown) therethrough. As will be further described, the device 100 has a first layer 140 and a second layer 150, each layer having a plurality of vent holes positioned along the length and width of the device 100 for ventilation.

As illustrated in FIG. 6, the device 100 includes a absorbent member 160 disposed on the interior 122 of an upper portion 120 of the retention body 130.

As shown in FIG. 5, the first layer 140 of the device 100 includes a plurality of vent holes 142 positioned along the length and width of the first layer 140 of the device 100. Likewise, and as best shown in FIG. 6, the second layer 150 includes a plurality of vent holes 152 positioned along the length and width of the second layer 150. Referring to FIG. 6 which shows a sectional view of the device 100. Preferably, the first and second layers 140, 150, include a plurality of dimples 147 selectively positioned and sandwiched between the first and second layers 140, 150. The dimples 147 cause a separation 148 between the layers 140, 150 and likewise between the vent holes 142 and 152 such to promote air circulation and ventilation between the layers 140, 150 and to allow air or ventilation to the inner chamber 135 of the retention body 130. As illustrated in FIG. 6, the dimples 147 are preferably equally spaced apart and again, form a continuous separation 148 between the layers 140, 150.

As illustrated, and as should be understood, the device 100 defines a generally cylindrical inner diameter surface interior for engaging the male. The device 100 as described is designed so that the user can fit the device 100 into position by directing the head of the penis through the lower opening 132 until the head of the penis is in contact with the absorbent member 160 disposed on the interior 122 of the upper portion 120. The inner chamber 135 of the retention body 130 envelopes the penis and is in fluid communication with the plurality of vent holes 142, 152.

The absorbent member 160 as described is positioned as an absorbing "shield" between the head of the penis and the user's trousers in order to collect any leakage that may occur once the device 100 is positioned as described.

The illustrative embodiment was designed for one-handed application. The inner chamber 135 of the retention body 130 provides a good anti-slip, fairly high-friction contact which they believe maintains the retention body 130 on the penis.

Preferably, the layers 140, 150, of the device 100 is constructed of a light weight, elastic or light rubber absorbent material however, other materials are also possible as long as the selected material provides comfort, sufficient strength and durability for the embodiment disclosed.

Although the description above contains many specificities, these should not be construed as limiting the scope of the invention but as merely providing illustrations of some of the presently preferred embodiments of this invention. Thus the scope of the invention should be determined by the appended claims in the formal application and their legal equivalents, rather than by the examples given.

I claim:

1. A device for men to manage the involuntary loss of bladder control, said device comprising:
   an upper portion integral to a lower portion, wherein the lower portion defines a retention body, said retention body having a lower opening to access an inner chamber sized and shaped to accommodate the insertion of a male penis,
   said upper portion defines an upper hood having an open position for exposing a head of the penis and a closed position for covering the head of the penis, such that the head of the penis can be exposed from the upper hood in the open position while the shaft of the penis remains enveloped in the lower portion,
   an absorbent member disposed on an interior of said upper hood for contact with the head of the penis when said upper portion is in the closed position,
   an attachment member that releasably secures the upper hood to the retention body in the closed position,
   said retention body including a first layer and a second layer, said first layer includes a plurality of vent holes positioned along the length and width of said first layer for ventilation and, said second layer includes a plurality of vent holes positioned along the length and width of said second layer for ventilation,
   said first and second layers further includes a plurality of dimples sandwiched between said first and second layers that form a separation between said layers for air circulation between said layers.

2. The device as recited in claim 1, wherein said inner chamber defines a generally cylindrical inner diameter surface interior.

3. The device as recited in claim 2, wherein said absorbent member is accessible when said upper hood is in the open position while the shaft of the penis remains enveloped in said retention body.

4. The device as recited in claim 3, wherein said first and second layers are constructed of a lightweight, elastic material.

5. The device as recited in claim 1, wherein said attachment member comprises a hook-and-loop connector.

6. A device for men to manage the involuntary loss of bladder control, said device comprising:
   a body having a lower opening to access an inner chamber sized and shaped to accommodate the insertion of a male penis, and an upper portion having an open position for exposing a head of the penis while a lower portion of the body envelops the penis, said upper portion also has a closed position for covering the head of the penis,
   a replaceable absorbent member disposed on an interior of said upper portion, wherein said replaceable absorbent member is configured to be replaced while the body envelops the penis,
   said body further including a first layer and a second layer, said first layer includes a plurality of vent holes positioned along the length and width of said first layer for ventilation and, said second layer includes a plurality of vent holes positioned along the length and width of said second layer for ventilation,
   said first layer further includes a plurality of dimples sandwiched between said first and second layers that form a separation between said layers for air circulation between said layers.

7. The device as recited in claim 6, wherein said inner chamber defines a generally cylindrical inner diameter surface interior.

8. The device as recited in claim 7, wherein said device further includes an attachment member that releasably secures the upper portion in the closed position.

9. The device as recited in claim 8, wherein said attachment member comprises a hook-and-loop connector.

10. The device as recited in claim 6, wherein said first and second layers are constructed of a lightweight, elastic material.

11. The device as recited in claim 6, wherein said first and second layers are constructed of a lightweight, rubber material.

* * * * *